United States Patent
Iwase (10) Patent No.: US 10,406,289 B2
(45) Date of Patent: Sep. 10, 2019

(54) DRUG INJECTION SYRINGE

(71) Applicant: Terumo Kabushiki Kaisha, Tokyo (JP)

(72) Inventor: Yoichiro Iwase, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 117 days.

(21) Appl. No.: 14/874,985

(22) Filed: Oct. 5, 2015

(65) Prior Publication Data
US 2016/0095978 A1    Apr. 7, 2016

Related U.S. Application Data

(63) Continuation of application No. PCT/JP2013/060433, filed on Apr. 5, 2013.

(51) Int. Cl.
*A61M 5/31* (2006.01)
*A61M 5/34* (2006.01)
(Continued)

(52) U.S. Cl.
CPC ............ *A61M 5/31* (2013.01); *A61M 5/3293* (2013.01); *A61M 5/345* (2013.01); *A61M 5/347* (2013.01);
(Continued)

(58) Field of Classification Search
CPC ...... A61M 5/31; A61M 5/3293; A61M 5/347; A61M 5/345; A61M 2005/3101
See application file for complete search history.

(56) References Cited

U.S. PATENT DOCUMENTS 2,371,086 A * 3/1945 Watson ................. A61M 5/282
                                                     604/192
3,035,616 A * 5/1962 Hamilton .............. A61M 5/344
                                                     141/329
(Continued)

FOREIGN PATENT DOCUMENTS

EP      2 554 201 A1    2/2013
JP     2002-177387 A    6/2002
(Continued)

OTHER PUBLICATIONS

Extended European Search Report and Search Opinion issued in EP Patent Application No. 13880969.4 dated Oct. 31, 2016.
(Continued)

*Primary Examiner* — Bradley J Osinski
(74) *Attorney, Agent, or Firm* — Foley & Lardner LLP (57) ABSTRACT

A drug injection syringe includes an injection needle assembly and a syringe body. The injection needle assembly includes an injection needle, a needle hub, an elastic body, and a fitting sleeve. The fitting sleeve accommodates the needle hub and the elastic body and has a fitting hole formed in a female taper shape. The syringe body includes an outer tube and a drug discharge tube formed in a male taper shape. The syringe body is attached to the injection needle assembly by pushing the drug discharge tube into the fitting hole by a press fitting. The elastic body couples the drug discharge tube and the injection needle in a liquid-tight manner by compressively deforming, due to the press fitting, at a protruding portion disposed on a periphery of the pocket and stretching against an inner wall of the fitting hole.

13 Claims, 6 Drawing Sheets

(51) Int. Cl.
*A61M 5/32* (2006.01)
*A61M 5/46* (2006.01)

(52) U.S. Cl.
CPC .............. *A61M 5/46* (2013.01); *A61M 5/349* (2013.01); *A61M 2005/3101* (2013.01)

(56) References Cited

U.S. PATENT DOCUMENTS

| | | | |
|---|---|---|---|
| 4,187,848 A | 2/1980 | Taylor | |
| 5,964,737 A | 10/1999 | Caizza | |
| 8,235,951 B2* | 8/2012 | Hund | A61M 5/3202 604/187 |
| 2011/0077602 A1* | 3/2011 | Yokota | A61M 5/32 604/239 |
| 2013/0079729 A1 | 3/2013 | Yokota et al. | |

FOREIGN PATENT DOCUMENTS

| | | |
|---|---|---|
| JP | 2011-212185 A | 10/2011 |
| WO | WO-2011/125561 A1 | 10/2011 |
| WO | WO-2012/157318 A1 | 11/2012 |

OTHER PUBLICATIONS

International Search Report issued in PCT/JP2013/060433 dated Jun. 25, 2013.
Chinese Office Action dated Nov. 13, 2018 in corresponding application No. 201380075214.9.

* cited by examiner

DRUG INJECTION SYRINGE

CROSS-REFERENCE TO RELATED PATENT APPLICATION

This application is a continuation application of and claims the benefit of priority to International Patent Application No. PCT/JP2013/060433, filed Apr. 5, 2013, the contents of which are herein incorporated by reference in its entirety.

TECHNICAL FIELD

The present invention relates to a drug injection syringe used for injecting a small amount of drug into an upper layer of skin.

BACKGROUND

A drug containing biologics, such as an influenza vaccine, is usually subcutaneously administered into a hypodermal tissue or intramuscularly administered into a muscular tissue deeper than a hypodermal tissue. Recently, it has been understood that a dosage of vaccine can be reduced by selecting an upper layer of skin, such as the epidermis and dermis, where a large number of immunocompetent cells exists as a target of vaccine administration. A skin includes an epidermis, which is a layer with a thickness of 50 to 200 µm from the surface of skin, a dermis, which is a layer with a thickness of 1.5 to 3.5 mm continuing from the epidermis, and a hypodermal tissue existing deeper than the dermis. The upper layer of skin is quite shallow to be targeted from the surface of a skin.

A known syringe for injecting a small amount of a drug into the upper layer of skin is configured with a tube body for containing the drug and an injection needle assembly including an injection needle, which are separately prepared. Immediately before injection, the injection needle assembly is attached to a drug discharge tube on the front end of the tube body.

For example, Japanese Patent Application Publication No. 2011-212185 ("Patent Literature 1") discloses a drug injection device including a tube body having a liquid chamber for containing a drug, a pusher configured with a gasket attached to a plunger so as to move inside the tube body, a tubular gripping portion provided around the outer periphery of the tube body, a connector connecting the tube body and the end portion of the gripping portion, and an injection needle assembly including an injection needle with a needle hub that holds a needle tube with an elastic body, where a drug discharge tube on the front end of the tube body is pushed into a fitting hole of the injection needle assembly to be attached.

The injection needle assembly is attached to the fitting hole by a taper fitting. Specifically, the drug discharge tube of the tube body is formed to have a male taper shape, in which the outer diameter gradually decreases toward the distal end. Meanwhile, the injection needle assembly is provided with a sleeve hole, or a fitting hole, formed to have a female taper shape that has a size corresponding to the drug discharge tube and in which the inner diameter gradually decreases from the opening of the fitting hole. The male taper and the female taper are formed to have the same taper ratio. When the drug discharge tube is pushed hard into the fitting hole, the taper surfaces are pressed against each other to be secured with a liquid-tight fit. In this state, the drug discharge tube on the front end of the tube body is exactly in contact with the elastic body inside a fitting sleeve of the tube body of the needle hub to prevent leakage.

SUMMARY

The male taper of the drug discharge tube and the female taper of the fitting hole are required to comply with the international standard of ISO 594-1:1986 (Conical fittings with a 6% (Luer) taper for syringes, needles and certain other medical equipment—Part 1: General requirements) and ISO 594-2:1998 (Conical fittings with 6% (Luer) taper for syringes, needles and certain other medical equipment—Part 2: Lock fittings). Taper ratios of these tapers are 6/100 taper when expressed in a fraction A/100, which indicates that the decrease in diameter is A mm per 100 mm.

Because the tube body and the injection needle assembly are parts formed of plastic, variations in dimension and taper ratio may occur during a forming process. The variation in dimension of a plastic part is no less than 0.03 mm, so that by taking the taper ratio and dimensional tolerances into consideration, a space with a gap as large as about 1 mm may be created between the drug discharge tube of the tube body and the elastic body. This space creates a dead volume of about 10 µL. Moreover, press fitting or threaded fitting is required in a taper fitting, in particular, in the Luer taper fitting, so that an additional dead volume of 0 to 30 µL, depending on a press fitting force or a tightening torque, is created.

The upper layer of skin includes a large volume of elastic fibrous tissues, such as elastin and collagen, and is thus firmer than the hypodermal tissue. When a large volume of drug is injected into the upper layer of skin, a patient feels an aching pain. As such, the volume of drug injected into the upper layer of skin should be as little as 200 µL or below, desirably about 100 µL. Thus, a total dead volume of 10 to 40 µL, which amounts to tens of percentages of costly and precious drug, such as vaccines and anticancer agents, is wasted during the injection of the drug. When priming is performed to prevent intrusion of air into a body, a further larger amount of drug is wasted. An injection volume of drug may vary by, for example, variation in the dead volume.

Certain embodiments of the present invention are made in view of the aforementioned problem. The object of certain embodiments of the present invention is to provide a drug injection syringe that allows an injection needle assembly to be surely attached to a tube body to prevent leakage even under a small attaching force, reduces the amount of a remaining drug by reducing a dead volume, and is capable of injecting a predetermined small amount of drug into a body with high efficiency.

A drug injection syringe according to certain embodiments of the present invention to achieve the object includes an injection needle assembly including an injection needle, a needle hub for supporting the injection needle, an elastic body mounted on the needle hub, the injection needle being inserted in the elastic body, and a fitting sleeve accommodating the needle hub and the elastic body and including an opened fitting hole formed in a female taper shape becoming thinner toward a needle tip. The drug injection syringe further includes a syringe body including an outer tube for containing a drug. The drug is sealed by a gasket inserted in the outer tube. The syringe body further includes a drug discharge tube provided on a front end side of the outer tube and is formed in a male taper shape to fit into the female taper. The syringe body is configured to be attached to the injection needle assembly by pushing the drug discharge tube into the fitting hole by a press fitting. The elastic body has a pocket that opens to a contact surface, which makes contact with a distal end of the drug discharge tube. The elastic body couples the drug discharge tube and the injection needle together in a liquid-tight manner by compressively deforming, by the press fitting, at a protruding portion provided on a periphery of the pocket to stretch against an inner wall of the fitting hole to provide liquid-tightness.

The drug injection syringe may be configured such that a gap is provided between the elastic body and the inner wall of the fitting hole, which allows the elastic body to compressively deform and stretch by the press fitting in order to provide liquid-tightness.

The drug injection syringe may be configured such that the elastic body is extended such that the contact surface is positioned closer to an opening of the fitting hole than a reachable distal end position of the male taper when it is fitted into the female taper. The elastic body is configured to compressively deform, while being in contact by the contact surface, by the press fitting, to stretch into the gap at the distal end position.

The drug injection syringe may be configured such that the elastic body stretches against the inner wall of the fitting hole and into the pocket at the protruding portion such that the pocket accommodates a needle root of the injection needle by the press fitting.

The drug injection syringe may be configured such that the elastic body accommodates the needle root of the injection needle in the pocket and has a portion projecting toward the needle root around the injection needle inside the pocket.

The drug injection syringe may be configured such that the elastic body couples the syringe body and the injection needle assembly together in a liquid-tight manner that withstands a pressure of no less than 3 MPa.

The drug injection syringe may be configured such that the drug discharge tube includes a locking mechanism including a threaded portion, the fitting hole is configured to screw with the threaded portion of the locking mechanism.

The drug injection syringe may be configured such that the fitting hole includes a guiding wall on the inner wall near the opening of the fitting hole formed by expanding the inner diameter.

The drug injection syringe may be configured such that, for example, the syringe body is a syringe prefilled with the drug and is to be connected to the injection needle assembly.

A drug injection syringe according to the present invention is configured such that, when an injection needle assembly is attached to a syringe body, an elastic body making contact with the distal end of a drug discharge tube compressively deforms by a press fitting in order to be forced to stretch against the inner wall of a fitting hole, and thereby the drug discharge tube and an injection needle are surely coupled together in a liquid-tight manner without leakage.

The elastic body is extended so as the contact surface, which makes contact with the distal end of the drug discharge tube, is positioned closer to the opening of the fitting hole than a distal end position of the male taper when the male taper is fitted in the female taper. By press fitting, the elastic body making contact with the distal end of the drug discharge tube compressively deforms to stretch against the inner wall of the fitting hole at the distal end. The compressive deformation of the elastic body fills a gap created by variations in dimension and taper ratio of the injection needle assembly and the syringe body, thereby providing compensation to reduce the dead volume caused by the gap.

This reduces an amount of remaining drug that cannot be ejected from the drug injection syringe. Thus, a predetermined small amount of drug can effectively be injected into a body. Accordingly, expensive drugs, such as vaccines and anticancer agents, can be properly injected into a body, in particular, into an upper layer of skin without waste.

The drug injection syringe is configured such that, even when the drug discharge tube is pushed into the fitting hole with a small force when attaching the injection needle assembly to the syringe body, the syringe body and the injection needle assembly are coupled together in a liquid-tight manner that withstands a pressure of no less than 3 MPa, so that no leakage of drug occurs.

If the fitting hole includes a guiding wall on the inner wall near the opening of the fitting hole formed by expanding the inner diameter, the expanded inlet for fitting allows the drug discharge tube to be inserted in the injection needle assembly easily.

The drug injection syringe is configured such that, if the drug discharge tube and the fitting hole have a locking mechanism, the injection needle assembly is surely pushed against the drug discharge tube to be tightly secured. Thus, the leakage of drug can be more surely prevented, and the injection needle assembly attached to the drug discharge tube can be more firmly supported.

DESCRIPTION OF THE EMBODIMENTS

Embodiments to carry out the present invention will be described below in detail. Note that the scope of the present invention is not limited to the embodiments.

Figures 1A, 1B:
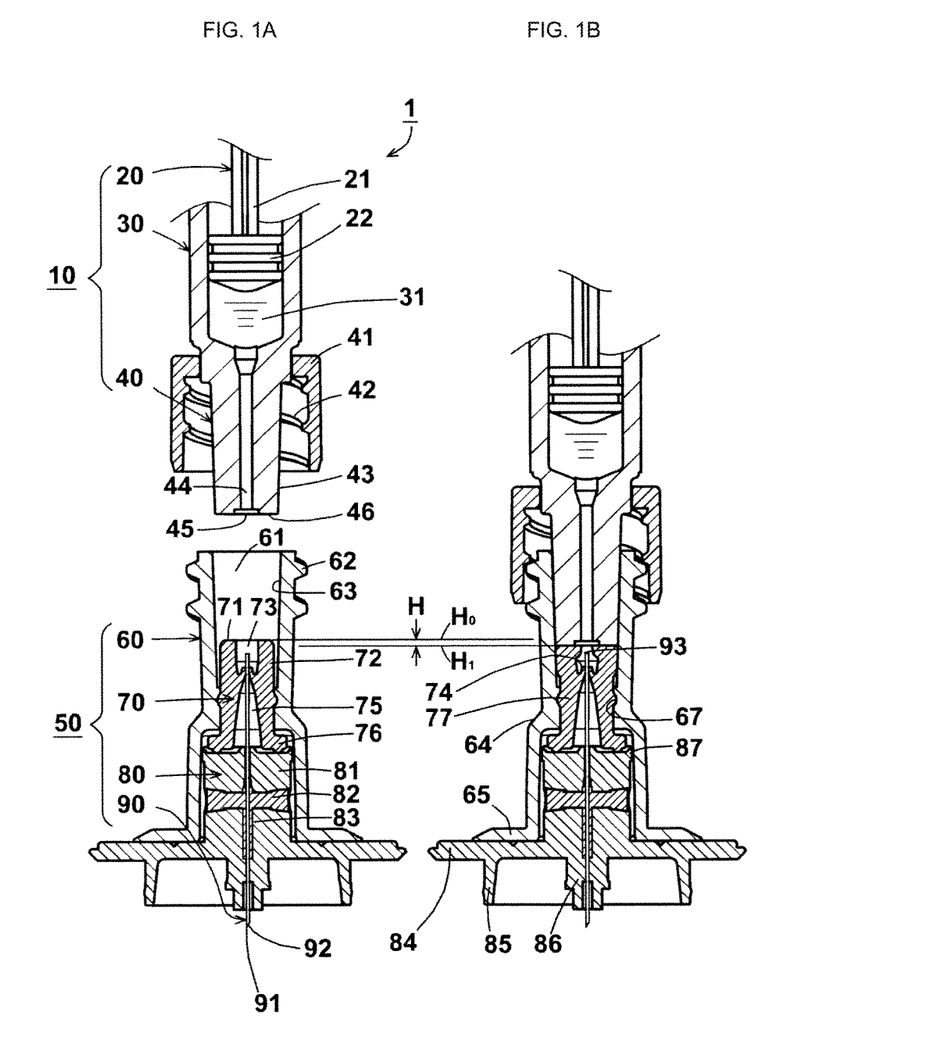
FIG. 1A and FIG. 1B are partial cross-sectional views, each illustrating a state in a procedure of using a drug injection syringe according to a first embodiment of the present invention.

A first embodiment of a drug injection syringe 1 according to the present invention will now be described with reference to FIGS. 1(a) and 1(b). FIGS. 1(a) and 1(b) are partial cross-sectional views, each illustrating a state in a procedure of using the drug injection syringe 1. The drug injection syringe 1 is used to pierce an upper layer of skin with a needle tip 91 to inject therein a small amount of drug 31.

The drug injection syringe 1 includes a syringe body 10 and an injection needle assembly 50 detachably attached to the syringe body 10. The syringe body 10 includes a pusher 20, an outer tube 30 having a cylindrical shape in which the pusher 20 is inserted, and a drug discharge tube 40 provided on the front end side of the outer tube 30. The injection needle assembly 50 includes an injection needle 90 having a needle tube, a needle hub 80 supporting the injection needle 90 with an injection needle holder 81, an elastic body 70 having an upper pocket 73 in which the injection needle 90 is inserted, and a fitting sleeve 60 that accommodates the elastic body 70 and the injection needle holder 81 of the needle hub 80 and has an opened fitting hole 61 formed to have a female taper 63. The elastic body 70 compressively deforms to reduce a dead volume and couples the drug discharge tube 40 and the injection needle 90 together in a liquid-tight manner.

First, the syringe body 10 will be described. The outer tube 30 of the syringe body 10 is formed into a hollow cylindrical shape that may be filled with the drug 31. The drug discharge tube 40 is coaxially provided in the center of the front end side of the outer tube 30. A gasket 22 is inserted in the outer tube 30 to force the drug 31 to be ejected from the drug discharge tube 40. The drug 31 is filled between the gasket 22 and the drug discharge tube 40. The gasket 22 seals the drug 31 inside the outer tube 30 in a liquid-tight manner to prevent leakage. A plunger 21 is connected to the proximal end side of the gasket 22 to constitute the pusher 20. A flange 32 is provided to extend in two directions from the outer periphery of the proximal end of the outer tube 30 (see FIG. 3). The drug discharge tube 40 includes a through-hole 44 from which the drug 31 inside the outer tube 30 is ejected outside the outer tube 30. The through hole 44 has a diameter of 0.8 to 1.2 mm and a length of 8 to 12 mm to reduce a dead volume thereinside. The outer circumference of the drug discharge tube 40 is formed in a male taper 43 in which the outer diameter decreases toward the tube front end and the taper ratio is 6/100 to comply with ISO 594-1 or ISO 594-2.

On its distal end, the drug discharge tube 40 includes a flat distal end face 46 normal to the axial direction. An opening 45 of the through-hole 44 is provided on and around the axis on the distal end face 46 to eject the drug 31. The opening 45 is larger than the diameter of the through-hole 44 by some degree. The outer profile of the distal end face 46 on the distal end of the drug discharge tube 40, that is the outer edge of the distal end of the drug discharge tube 40, is formed in a circular shape. The distal end face 46 of the drug discharge tube 40 and the surface of the male taper 43 of the drug discharge tube 40 continuously meet at the outer edge of the distal end of the drug discharge tube 40. The distal end face 46 of the drug discharge tube 40 has an area sufficient to make contact with and compressively deform the elastic body 70 inside the fitting sleeve 60. The distal end face 46 of the drug discharge tube 40 comes into surface contact with a top end face 71 of a protruding portion 72 provided to circumferentially surround the upper pocket 73 of the elastic body 70 in order to couple the drug discharge tube 40 and the injection needle 90 together in a liquid-tight manner. This provides an effect of reducing the dead volume created between the drug discharge tube 40 and the elastic body 70 and between the drug discharge tube 40 and the fitting sleeve 60. The drug discharge tube 40 is sealed by a drug discharge tube cap 11 (see FIG. 3) until just before the injection to prevent leakage of the drug 31, which may result in contamination of external bacteria.

The drug discharge tube 40 includes on the rear end side thereof a locking mechanism 41 having a sleeve coaxially surrounding the drug discharge tube 40. The sleeve of the locking mechanism 41 has a cross-section with a circular inner circumference and, for example, a pentagonal outer circumference that is easily held and turned. The locking mechanism 41 is provided as a separate member from the outer tube 30 and the drug discharge tube 40 and attached by, for example, bonding, fitting, or screwing, to be further on the proximal end side than the drug discharge tube 40. Alternatively, the locking mechanism 41 is integrally formed with the outer tube 30 or the drug discharge tube 40. The locking mechanism 41 has on the cylindrical inner wall a threaded portion, such as an internal thread 42. The internal thread 42 can be screwed onto the drug discharge tube cap 11 or an external thread 62 of the fitting sleeve 60. When press fitting the drug discharge tube 40 into the fitting hole 61 of the fitting sleeve 60, the drug discharge tube 40 can tightly fit into the fitting hole 61 of the fitting sleeve 60 as the locking mechanism 41 is screwed deeper. As the locking mechanism 41 is screwed deeper, the distal end face 46 of the drug discharge tube 40 pushes the protruding portion 72 of the elastic body 70 harder. Even when the drug discharge tube 40 is tightly press fitted into the fitting hole 61 of the fitting sleeve 60, the deformation of the male taper 43 and the female taper 63 is limited, such that a distal end position by the fitting, $H_1$, corresponds to and is determined by the taper ratios, dimensional tolerances, materials of the drug discharge tube 40 and the fitting sleeve 60 and the degree of tightening the locking mechanism 41.

The injection needle assembly 50 will now be described. FIG. 1A illustrates the syringe body 10 just before being attached and coupled to the injection needle assembly 50.

The injection needle 90 includes a hollow needle tube. The injection needle 90 further includes a needle tip 91 that protrudes from the injection needle assembly 50 and has a bladed edge 92 with an acute angle to the axis to pierce a skin, and a needle root 93 that is accommodated inside the injection needle assembly 50 and formed in a face approximately perpendicular to the axis. The length along the axial direction of the bladed edge 92 of the injection needle 90 is 0.5 to 1.4 mm. When expressed by ISO standard for a needle tube for medical use (ISO 9626:1991/Amd. 1:2001(E)), the injection needle 90 may be a needle tube having a gauge size of 26 to 33 (outer diameter of 0.2 to 0.45 mm), preferably 30 to 33. By using such an injection needle 90, an aching pain felt by a patient when injecting the drug 31 into the upper layer of skin is alleviated and the dead volume of the drug 31 remaining inside a hollow of the needle tube can be minimized. As a material of the injection needle 90, stainless steel, for example, may be used. Although, the material is not limited to stainless steel, and aluminum, an aluminum alloy, titanium, a titanium alloy, or other metals may be used. In addition, a straight needle or a tapered needle having at least a portion of which is tapered may be used as the injection needle 90.

The injection needle 90 penetrates the center of the needle hub 80 to be held therein. The needle hub 80 is integrally configured with an injection needle holder 81, an adjusting portion 86, a holding portion 85, and a connection guiding portion 84. The injection needle holder 81 has an approximately column shape and holds the injection needle 90 in the needle root 93 side (see the upper part of FIGS. 1(a) and 1(b)). The adjusting portion 86 helps with the injection of the drug 31 from the injection needle 90 in the needle tip 91 side (see the lower part of FIGS. 1(a) and 1(b)). The holding portion 85 surrounds the adjusting portion 86. The connection guiding portion 84 supports the adjusting portion 86 and the holding portion 85 and continues to the injection needle holder 81. The injection needle 90 coaxially penetrates the injection needle holder 81 and the adjusting portion 86 in the center thereof with the needle tip 91, including the bladed edge 92, protruding from the adjusting portion 86 and the needle root 93 protruding in the opposite direction from the injection needle holder 81. In the middle of the body portion of the injection needle holder 81 having an approximately cylindrical shape, a symmetric adhesive filling side hole 82 penetrating the side wall to the axis and an adhesive filling cavity 83 having an approximately cylindrical shape surrounding the injection needle 90 and continuing to the adhesive filling side hole 82 are provided. An adhesive filled in the adhesive filling hole 82 and the adhesive filling cavity 83 is cured to fix the injection needle 90. The rim of the end portion of the injection needle holder 81 in the needle root 93 side slightly projects and has a slightly large outer diameter.

The elastic body 70 is mounted on the injection needle holder 81 of the needle hub 80 and is positioned inside the inner edge of the projecting rim on the end portion of the injection needle holder 81 on the needle root 93 side. The injection needle 90 is inserted through the axis of the elastic body 70 from the needle root 93 side. The elastic body 70 has a brim 76 on the end portion on the needle tip 91 side. The elastic body 70 includes a lower pocket 75 formed in an approximately conical hollow manner, which accommodates the injection needle 90. The elastic body 70 includes an upper pocket 73 formed as a cylindrical depression, which accommodates the needle root 93 side of the injection needle 90. The top end face 71 of the protruding portion 72 circumferentially surrounding the upper pocket 73 is approximately flat. The top end face 71 of the protruding portion 72 has an area sufficient to come into a surface contact with the distal end face 46 of the drug discharge tube 40. The opening diameter of the upper pocket 73 of the elastic body 70 is equal to or smaller than the diameter of the opening 45 provided on the distal end of the drug discharge tube 40. With the top end face 71 of the protruding portion 72 in surface contact with the distal end face 46 of the drug discharge tube 40, the drug discharge tube 40 is pushed into the fitting hole 61 of the fitting sleeve 60 by a press fitting, which compressively deforms the protruding portion 72, thereby coupling the drug discharge tube 40 and the injection needle 90 together in a liquid-tight manner. This gives an effect of reducing the dead volume created between the drug discharge tube 40 and the elastic body 70 and between the drug discharge tube 40 and the fitting sleeve 60 (see FIG. 1B)). The central portion of the upper end pocket 73 projects toward the needle root 93 side around the injection needle 90 to form a valve portion 74 that gives uniform pressure on the circumference of the injection needle 90. The injection needle 90 is supported by the portion of the elastic body 70 between the upper pocket 73 and the lower pocket 75. The needle root 93 of the injection needle 90 is accommodated in the upper pocket 73 and slightly shifted to the needle tip 91 side from the top end face 71 of the protruding portion 72. The elastic body 70 includes a ring 77 swelling outward in a ring shape from the outer circumference of the body portion of the elastic body 70.

The elastic body 70 and the injection needle holder 81 of the needle hub 80 are covered by the fitting sleeve 60 to be accommodated therein. The fitting sleeve 60 has a brim 65 on the bottom end. The fitting sleeve 60 is integrated with the connection guiding portion 84 of the needle hub 80 by bonding or welding, or alternatively, by integral forming. The fitting sleeve 60 has a shoulder portion 64 in the middle portion where the diameter decreases to be smaller than the lower half of the fitting sleeve 60. The injection needle holder 81 of the needle hub 80 is accommodated in the lower half of the fitting sleeve 60. A large diameter portion 87 having a slightly large outer diameter on the end portion in the needle root 93 side of the injection needle holder 81 of the needle hub 80 makes contact with the inner wall of the lower half of the fitting sleeve 60 to prevent slip. The fitting sleeve 60 encompasses or presses the brim 76 of the elastic body 70 with the shoulder portion 64. The fitting sleeve 60 has on the inner wall near the shoulder portion 64 an annular recess 67 that is depressed radially outward in an annular form. The ring 77 on the outer circumference of the elastic body 70 engages with the annular recess 67. The fitting sleeve 60 has an opening on the top end. The inner diameter of the fitting sleeve 60 continuously decreases from the opening down to the annular recess 67. The fitting hole 61 is formed to have the female taper 63 tapering toward the bottom end side with a taper ratio of 6/100.

The female taper 63 of the fitting hole 61 and the male taper 43 of the drug discharge tube 40 have the same taper ratio. Thus, by pushing the drug discharge tube 40 into the fitting hole 61 by a press fitting, the syringe body 10 can be tightly coupled with the injection needle assembly 50. As the drug discharge tube 40 is pushed harder into the fitting hole 61, the drug discharge tube 40 and the fitting hole 61, both made of plastic, slightly deform to be fit deeper.

In the injection needle assembly 50, both the male taper 43 and the female taper 63 are adjusted such that $H_1$, which is a reachable distal end position of the taper by fitting the male taper 43 of the drug discharge tube 40 into the female taper 63 of the fitting sleeve 60, reaches a position lower, or closer to the needle tip 91, than the top end face 71 of the protruding portion 72 of the elastic body 70 by a height difference of H when the elastic body 70 does not exist in the fitting sleeve 60. Therefore, the elastic body 70 is previously formed such that the top end face 71 of the protruding portion 72 of the elastic body 70, which is allowed to make contact with the distal end face 46 of the drug discharge tube 40, is positioned to be closer to the opening of the fitting hole 61 than $H_1$, which is the reachable distal end position of the taper by fitting the male taper 43 into the female taper 63, by the height difference of H, that is, to be at $H_0$, which is a position of the top end face before the fitting, when the syringe body 10 is not yet attached to the injection needle assembly 50 as illustrated in FIG. 1A. As illustrated in FIG. 1B, the volume, the height, and the shape of the protruding portion 72 is suitably adjusted such that, by pushing the drug discharge tube 40 into the fitting hole 61 by a press fitting, the elastic body 70 in the fitting sleeve 60 makes contact with the distal end face 46 of the drug discharge tube 40 by the top end face 71 of the protruding portion 72 and compressively deforms at the protruding portion 72 so as the protruding portion 72 stretches outward against the inner wall of the fitting hole 61, thereby providing liquid-tightness. Preferably, the protruding portion 72 is adjusted such that the protruding portion 72 compressively deforms, by the press fitting, to stretch not only against the inner wall of the fitting hole 61, but also into the upper pocket 73, thereby providing liquid-tightness.

Due to variations in dimension and taper ratio occurring when forming the syringe body 10 and the injection needle assembly 50, a gap is possibly created between the male taper 43 of the drug discharge tube 40 and the female taper 63 of the fitting sleeve 60 and between the female taper 63 of the fitting sleeve 60 and the elastic body 70. A gap is always created in the upper pocket 73. However, the gaps are closed by compressive deformation of the elastic body 70 when the drug discharge tube 40 is pushed into the fitting hole 61 of the fitting sleeve 60 by the press fitting, thereby compensating for the dead volume.

The external thread 62 is provided on the outer circumference of the fitting sleeve 60 to be screwed into the internal thread 42 of the locking mechanism 41.

If the fitting hole 61 of the fitting sleeve 60 has a guiding wall (not shown) on the inner wall near the opening formed by expanding the inner diameter, the drug discharge tube 40 can be easily inserted in the fitting hole 61 with no interference.

The injection needle holder 81 of the needle hub 80 is connected to the connection guiding portion 84, which is formed in a disk shape extending from the needle tip 91 side of the needle hub 80. The connection guiding portion 84 has a larger diameter than the injection needle holder 81. The injection needle 90 penetrates the injection needle holder 81 and the column-shaped adjusting portion 86, which are coaxially provided, protruding to the needle tip 91 side from the connection guiding portion 84. The adjusting portion 86 has a depression in the needle tip 91 side to help the injection of the drug 31 from the injection needle 90 by stretching an epidermis during the drug injection. The needle tip 91 of the injection needle 90 protrudes from the center of the depression. The end face of the adjusting portion 86 in the needle tip 91 side is sufficiently small compared to the size of a blister generated when injecting the drug 31 into an upper layer of skin.

The holding portion 85 has a hollow cylindrical shape surrounding the adjusting portion 86 and a diameter larger than the adjusting portion 86 and the injection needle holder 81 but smaller than the connection guiding portion 84. The holding portion 85 protrudes from the connection guiding portion 84 to the needle tip 91 side. On injecting the drug, the surface of the skin makes contact with, in sequence, the bladed edge 92 of the injection needle 90, the end face of the adjusting portion 86 in the needle tip 91 side, and the holding portion 85. The space between the adjusting portion 86 and the holding portion 85 stretches the surface of the skin to allow the injection needle 90 to pierce the upper layer of skin along an approximately upright direction.

On injecting the drug 31, the connection guiding portion 84, having a larger diameter than the holding portion 85, makes contact with the surface of the skin with a sufficient area to prevent a slip of the drug injection syringe 1.

The syringe body 10 and its locking mechanism 41, the fitting sleeve 60 and the needle hub 80 of the injection needle assembly 50, and the plunger of the pusher 20 are formed of plastics, such as a thermoplastic resin and a thermoset resin, and/or metals. The plastics may include polypropylene, polycarbonate, polyethylene, and cycloolefin polymer. The metals may include stainless steel and aluminum. The elastic body 70 and the gasket 22 are formed of rubbers, such as natural rubber and silicone rubber, thermoplastic elastomers, such as polyurethane-based elastomer and styrene-based elastomer, or an elastic material of a combination thereof.

An injection needle assembly cap 51 (see FIG. 3) is attached to the injection needle assembly 50 to cover the whole needle tip 91 of the injection needle 90 until the injection needle assembly 50 is attached to the syringe body 10 just before injecting the drug 31.

The drug injection syringe 1 is manufactured as described below. First, the injection needle assembly 50 is manufactured as described below. The fitting sleeve 60 and the needle hub 80 are each formed of a plastic material, and the elastic body 70 is formed of a rubber material. The injection needle 90 is inserted in the coaxially-provided penetrating holes of the injection needle holder 81 and the adjusting portion 86 of the needle hub 80. With the needle tip 91 of the injection needle 90 protruding from the adjusting portion 86 by a desired length for piercing a skin, an adhesive is injected from the adhesive filling side hole 82 formed in the injection needle holder 81 to bond together and fix the injection needle holder 81 and the injection needle 90. The elastic body 70 is inserted in the fitting sleeve 60 to engage the brim 76 of the elastic body 70 with the shoulder portion 64 of the fitting sleeve 60. An adhesive is applied to the contact portion between the brim 65 of the fitting sleeve 60 and the connection guiding portion 84 of the needle hub 80. The needle hub 80 together with the injection needle 90 is inserted in the fitting sleeve 60, piercing through the elastic body 70 from the needle root 93 side of the injection needle 90. Then the brim 65 of the fitting sleeve 60 and the connection guiding portion 84 of the needle hub 80 are bonded together and fixed to constitute the injection needle assembly 50. The injection needle assembly 50 is contained in the injection needle assembly cap 51 to be enclosed and sealed by thermally welding a cover and sterilized as required.

Meanwhile, the syringe body 10 is manufactured as described below. The outer tube 30, the drug discharge tube 40, and the locking mechanism 41 are each formed from a plastic material in an integrated manner. After forming the gasket 22 of a rubber material and forming the plunger 21 of a plastic material, the gasket 22 is connected to the plunger 21 to constitute the pusher 20. The syringe body 10 is sealed with the drug discharge tube cap 11, and then the outer tube 30 of the syringe body 10 is filled with the drug 31. The filled amount of the drug 31 is, for example, a desired amount to be injected into an upper layer of skin (for example, 100 to 200 µL) plus a slight amount of a resulting dead volume (total amount of 110 to 150 µL). After filling such an amount of the drug 31, the gasket 22 of the pusher 20 is inserted together with the plunger 21 to constitute a prefilled syringe, that is, the syringe body 10. The syringe body 10 is sealed in a sterile bag and sterilized as required.

Now, a method of coupling together the syringe body 10 and the injection needle assembly 50 by pushing the drug discharge tube 40 into the fitting hole 61 of the fitting sleeve 60 by a press fitting and injecting the drug 31 into an upper layer of skin will be described.

Figure 2:
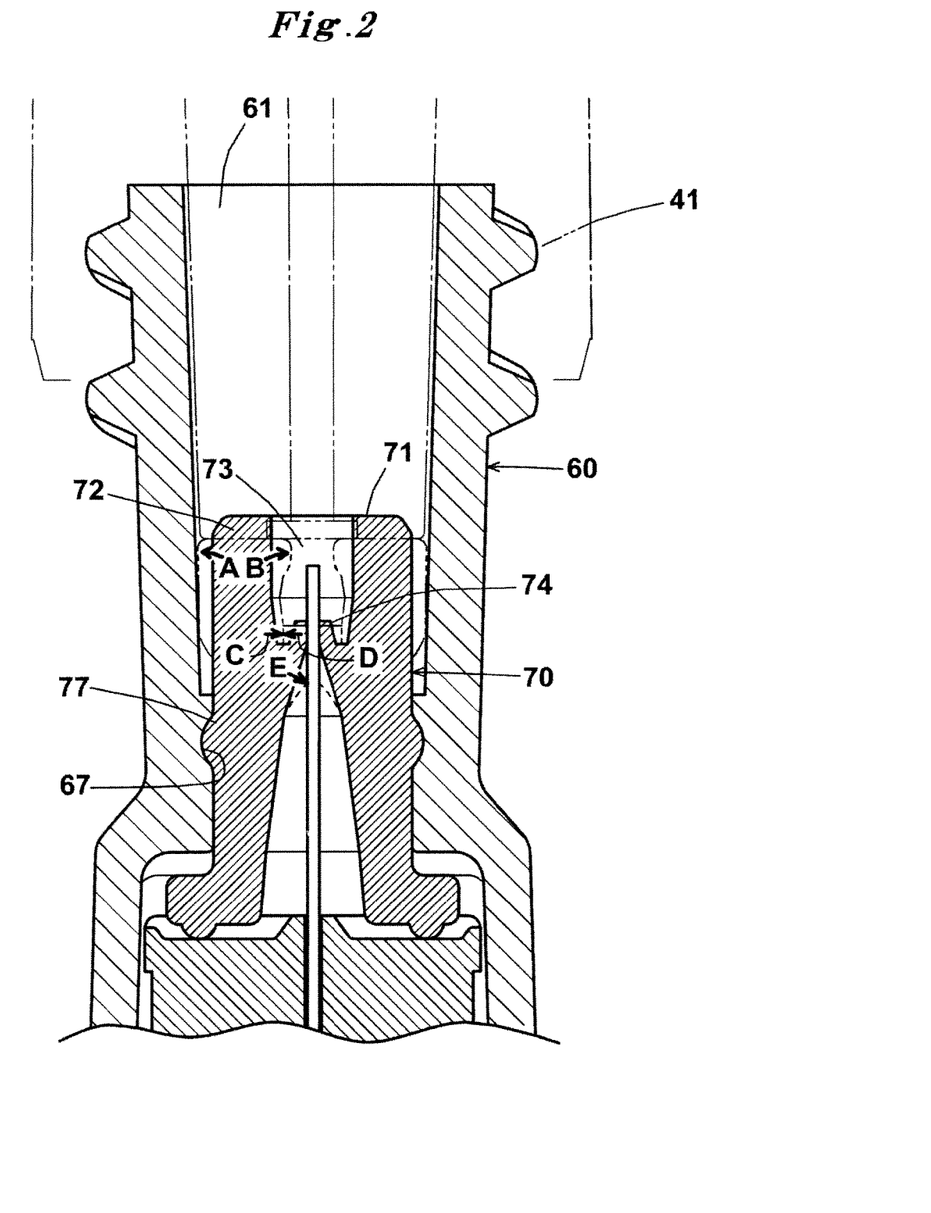
FIG. 2 is a partially enlarged view illustrating the drug injection syringe.
Figure 3:
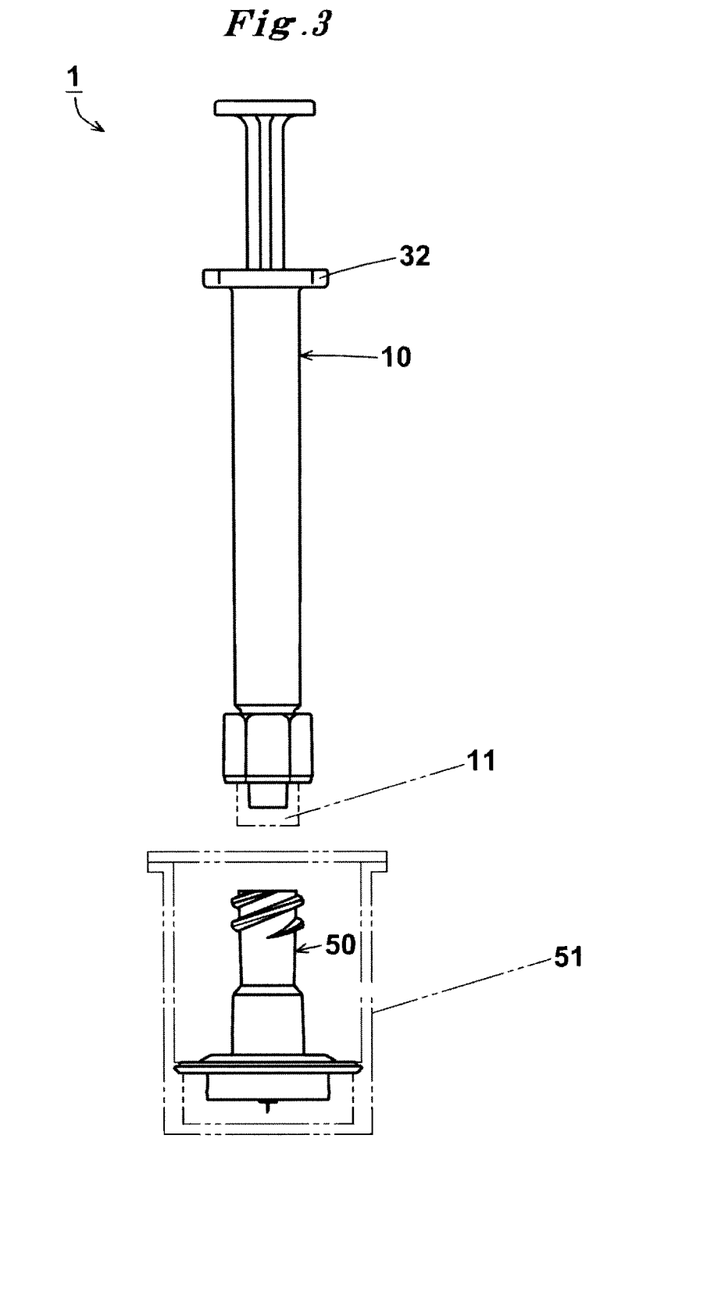
FIG. 3 is an exploded side view illustrating the drug injection syringe.

The syringe body 10 and the injection needle assembly 50 are unsealed (see FIG. 3). As illustrated in FIGS. 1(a) to 2, the drug discharge tube 40 of the syringe body 10 is pushed softly into the fitting hole 61 of the fitting sleeve 60 of the injection needle assembly 50, then the internal thread 42 of the cylindrical locking mechanism 41 surrounding the drug discharge tube 40 is screwed onto the external thread 62 of the fitting sleeve 60 of the injection needle assembly 50, and then tightening starts at a small torque of about 0.03 to 0.1 N·m. Now, the drug discharge tube 40 is inserted deeper into the fitting hole 61 of the fitting sleeve 60.

As the locking mechanism 41 is further tightened, first, the distal end face 46 of the drug discharge tube 40 makes contact with the top end face 71 of the protruding portion 72 of the elastic body 70 exactly upon reaching $H_0$, which is the position of the top end face before the fitting. When the locking mechanism 41 is further tightened, the internal thread 42 and the external thread 62 are screwed deeper, and the distal end face 46 of the drug discharge tube 40 in contact with the protruding portion 72 of the elastic body 70 pushes the protruding portion 72 hard, thereby causing the compressive deformation of the protruding portion 72 to begin. When the locking mechanism 41 is further tightened, the protruding portion 72 is pushed much harder by the top end face 71 and eventually the male taper 43 of the drug discharge tube 40 fully fits against the female taper 63 of the fitting hole 61 of the fitting sleeve 60. Now, further tightening cannot be made. The protruding portion 72 of the elastic body 70 has compressively deformed to the degree such that the top end face 71 is at $H_1$, which is the reachable distal end position of the taper by fitting the male taper 43 into the female taper 63. The height difference H, that is, the difference of length before and after the compressive deformation, is preferably 0.2 to 3.0 mm.

As illustrated in FIG. 2, since the ring 77 on the outer circumference of the elastic body 70 engages with the annular recess 67 on the inner wall of the fitting sleeve 60, the compressive deformation of the elastic body 70 mainly takes place in the portion between the top end face 71 of the protruding portion 72 and the ring 77. As indicated by an arrow A in FIG. 2, the protruding portion 72 of the elastic body 70 stretches outward against the inner wall of the fitting hole 61 of the fitting sleeve 60 to fill the gap created between the elastic body 70 and the fitting sleeve 60, thereby providing liquid-tightness and almost eliminating the dead volume in this region. As indicated by arrows B and C in the same figure, the protruding portion 72 of the elastic body 70 is stretched inward into the upper pocket 73 of the elastic body 70. The volume of the upper pocket 73 decreases by the compressive deformation and further by the stretching of the protruding portion 72 of the elastic body 70, so that the dead volume in this region is reduced. As indicated in arrows C, D, and E in the same figure, in the upper pocket 73 of the elastic body 70, the valve portion 74 formed by projecting around the injection needle 90 toward the needle root 93 tightly presses the circumference of the injection needle 90 by the compressive deformation of the protruding portion 72, and thus the protruding portion 72 of the elastic body 70 further enhances liquid-tightness. In this manner, the protruding portion 72 of the elastic body 70 fills the gap created between the elastic body 70 and the fitting sleeve 60 and the gap in the upper pocket 73, thereby providing liquid-tightness. As a result, the drug discharge tube 40 and the injection needle 90 can be coupled together in a liquid-tight manner, and at the same time, the dead volume can be minimized.

Then the injection needle assembly cap 51 is taken off. The needle tip 91 of the injection needle assembly 50 is pointed to a skin. The drug injection syringe 1 is pushed onto the skin with the injection needle 90 positioned vertical to the skin. The needle tip 91 pierces the skin, and the holding portion 85 is pushed onto the skin. The adjusting portion 86 touches the skin, and the holding portion 85 and the adjusting portion 86 stretch the skin. As the bladed edge 92 of the needle tip 91 exactly reaches the upper layer of skin, the pusher 20 is fully pushed through to inject the drug 31. In this state, since the elastic body 70 has sufficiently deformed by compression, the elastic body 70 does not further deform by the pressure applied to the drug 31 by the pusher 20. Because the dead volume in the drug injection syringe 1 is minimized, the amount of the drug 31 remaining in the drug injection syringe 1 is very small. Then the injection needle 90 is pulled out to remove the drug injection syringe 1 from the skin. The drug injection syringe 1 is sealed again with the injection needle assembly cap 51 and disposed as medical waste.

Figure 4:
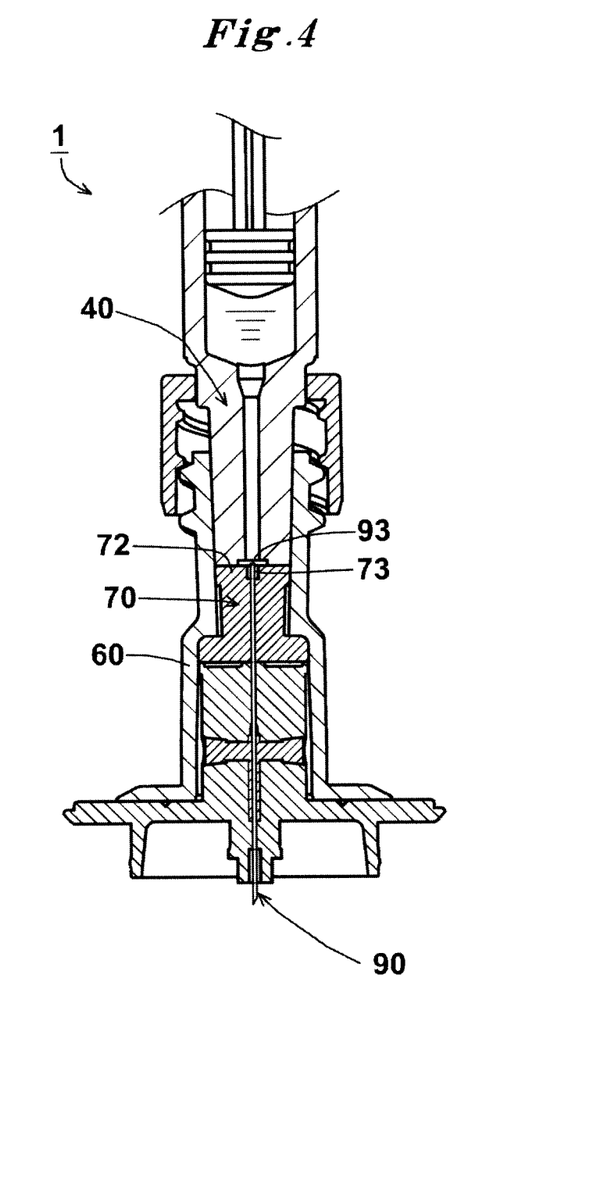
FIG. 4 is a partial cross-sectional view illustrating a state in a procedure of using a drug injection syringe according to a second embodiment of the present invention.

A second embodiment of the drug injection syringe 1 according to the present invention is illustrated in FIG. 4. The drug injection syringe 1 has the same configuration as that illustrated in FIGS. 1(a) to 2 except for the shape of the elastic body 70. The difference in the shape of the elastic body 70 is that an upper pocket 73 provided around the needle root 93 of the injection needle 90 is formed in an approximately cylindrical bore having a diameter of about the size of the diameter of the injection needle 90 and that no lower pocket 75 is provided. The small space in the upper pocket 73 allows the protruding portion 72 of the elastic body 70 to compressively deform in a manner that the protruding portion 72 of the elastic body 70 is sufficiently stretched against the inner wall of the fitting sleeve 60 to eventually connect together the drug discharge tube 40 and the injection needle 90 in a liquid-tight manner. Note that, a lower pocket 75 may be provided around the injection needle 90 in an approximately conically shaped pocket having a diameter about the size of the diameter of the injection needle.

Figure 5:
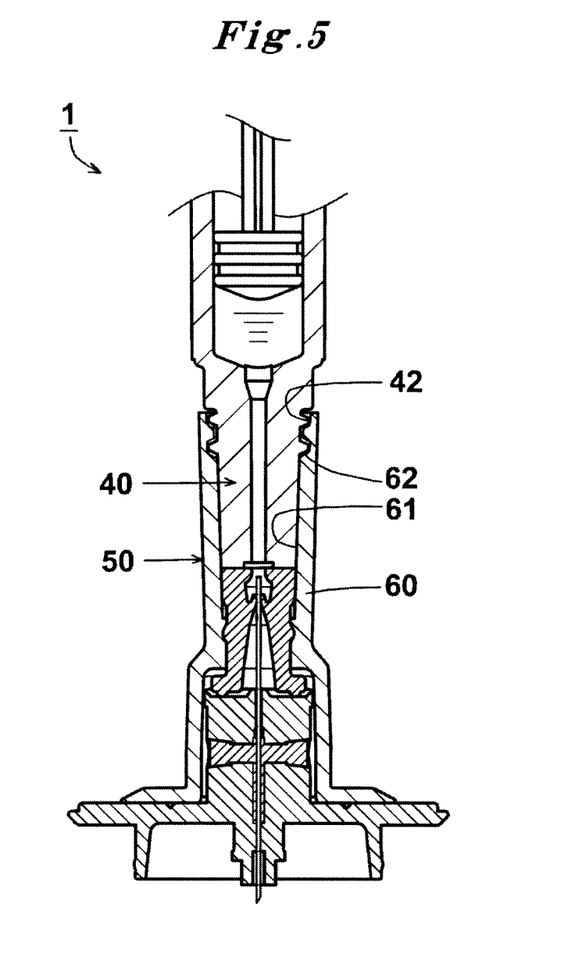
FIG. 5 is a partial cross-sectional view illustrating a state in a procedure of using a drug injection syringe according to a third embodiment of the present invention.

A drug injection syringe 1 according to a third embodiment, as illustrated in FIG. 5, includes a threaded portion 42 serving as a locking mechanism 41 formed on an outer periphery of the drug discharge tube 40 in the proximal end side and a threaded portion 62 formed on the inner wall of the fitting hole 61 of the fitting sleeve 60 of the injection needle assembly 50. In this example, the threaded portion is an external thread and the threaded portion is an internal thread. In the drug injection syringe 1, the threaded portions are screwed together inside the fitting hole 61 of the fitting sleeve 60.

Figure 6:
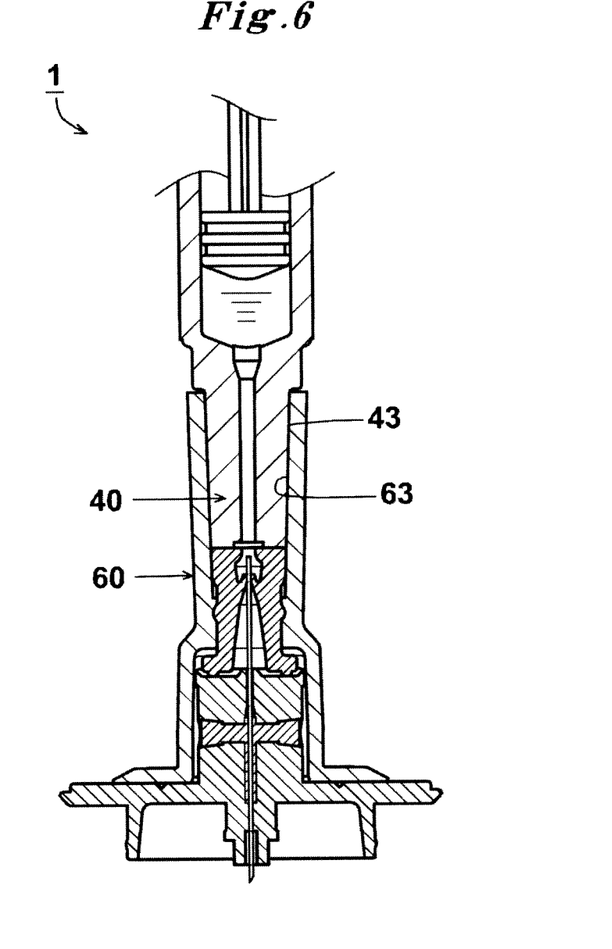
FIG. 6 is a partial cross-sectional view illustrating a state in a procedure of using a drug injection syringe according to a fourth embodiment of the present invention.

An example drug injection syringe 1 according to a fourth embodiment, as illustrated in FIG. 6, includes a drug discharge tube 40 having no locking mechanism and a fitting sleeve 60 of an injection needle assembly having no threaded portion. In the drug injection syringe 1, the male taper 43 of the drug discharge tube 40 is fixed to the female taper 63 of the fitting sleeve 60 only by the fitting.

The threaded portion 42 of the locking mechanism 41 included in the drug discharge tube 40 and the threaded portion 62 included in the injection needle assembly 50 are not limited to the examples described above. Any configuration can be used that has an external thread or an internal thread formed in a section of the drug discharge tube 40 to serve as the locking mechanism 41 and an internal thread or an external thread, corresponding to the locking mechanism 41, formed in a section of the fitting sleeve 60.

The shape of the locking mechanism 41 or whether the locking mechanism 41 is required may suitably be determined according to the gauge size of the injection needle 90 or an injection pressure.

A drug injection syringe according to the present invention is used for injecting a small amount of drug into an upper layer of skin of a patient.

What is claimed is:

1. A drug injection syringe comprising:
   an injection needle assembly comprising:
      an injection needle,
      a needle hub supporting the injection needle,
      an elastic body disposed on the needle hub, wherein the injection needle is disposed in the elastic body, and
      a fitting sleeve accommodating the needle hub and the elastic body, and including a fitting hole formed in a female taper shape having a diameter that decreases toward a needle tip; and
   a syringe body comprising:
      an outer tube configured to contain a drug sealed by a gasket disposed in the outer tube, and
      a drug discharge tube provided on a distal end side of the outer tube, wherein the drug discharge tube has a male taper shape configured to fit in the female taper shape of the fitting sleeve,
      wherein the syringe body is configured to be attached to the injection needle assembly by press fitting the drug discharge tube into the fitting hole,
   wherein the elastic body comprises a protruding portion that has a contact surface configured to make contact with a distal end of the drug discharge tube, the protruding portion defining a pocket that opens at the contact surface, and the protruding portion being spaced from an inner wall of the fitting hole by a gap that allows the elastic body to compressively deform, and wherein, when the drug discharge tube is press fit into the fitting hole: (i) the elastic body couples the drug discharge tube and the injection needle in a liquid-tight manner by the protruding portion compressively deforming against the inner wall of the fitting hole, (ii) the elastic body is deformed further radially inward at a proximal end of the pocket than at a distal end of the pocket and (iii) a proximal-most end of the injection needle is located in the pocket defined by the protruding portion.

2. The drug injection syringe according to claim 1, wherein the elastic body is configured to be extended such that the contact surface is positioned closer to an opening of the fitting hole than a reachable distal end position of the male taper shape when the male taper shape is fitted into the female taper shape, and wherein the elastic body is configured to compressively deform into the gap at the reachable distal end position when the drug discharge tube is press fit into the fitting hole.

3. The drug injection syringe according to claim 1, wherein the elastic body comprises a projecting portion at a distal end side of the pocket that contacts and holds the injection needle and projects toward the proximal-most end of the injection needle.

4. The drug injection syringe according to claim 1, wherein the elastic body is configured to couple the syringe body and the injection needle assembly in a liquid-tight manner that withstands a pressure of no less than 3 MPa.

5. The drug injection syringe according to claim 1, wherein the drug discharge tube comprises a locking mechanism including a threaded portion, and wherein the fitting hole is configured to screw with the threaded portion of the locking mechanism.

6. The drug injection syringe according to claim 1, wherein the fitting hole comprises a guiding wall on the inner wall near the opening of the fitting hole formed by expanding an inner diameter of the inner wall.

7. The drug injection syringe according to claim 1, wherein the syringe body is a syringe prefilled with the drug and configured to be connected to the injection needle assembly.

8. An injection needle assembly configured to be attached to a syringe body that includes a drug discharge tube, the injection needle assembly comprising:
    an injection needle;
    a needle hub supporting the injection needle;
    an elastic body disposed on the needle hub, wherein the injection needle is disposed in the elastic body; and
    a fitting sleeve accommodating the needle hub and the elastic body, and including a fitting hole formed in a female taper shape having a diameter that decreases toward a needle tip; and wherein the elastic body comprises a protruding portion that has a contact surface configured to make contact with a distal end of the drug discharge tube, the protruding portion defining a pocket that opens at the contact surface, and the protruding portion being spaced from an inner wall of the fitting hole by a gap that allows the elastic body to compressively deform, and wherein, when the drug discharge tube is press fit into the fitting hole, the elastic body couples the drug discharge tube and the injection needle in a liquid-tight manner by the protruding portion compressively deforming against the inner wall of the fitting hole: (ii) the elastic body is deformed further radially inward at a proximal end of the pocket than at a distal end of the pocket, and (iii) a proximal-most end of the injection needle is located in the pocket defined by the protruding portion.

9. The injection needle assembly according to claim 8, wherein the elastic body is configured to be extended such that the contact surface is positioned closer to an opening of the fitting hole than a reachable distal end position of a male taper shape of the drug discharge tube when the male taper shape is fitted into the female taper shape, and wherein the elastic body is configured to compressively deform into the gap at the reachable distal end position when the drug discharge tube is press fit into the fitting hole.

10. The injection needle assembly according to claim 8, wherein the elastic body comprises a projecting portion at a distal end side of the pocket that contacts and holds the injection needle and projects toward the proximal-most end of the injection needle.

11. The injection needle assembly according to claim 8, wherein the elastic body is configured to couple the syringe body and the injection needle assembly in a liquid-tight manner that withstands a pressure of no less than 3 MPa.

12. The drug injection syringe according to claim 8, wherein the fitting hole is configured to screw with a threaded portion of a locking mechanism of the drug discharge tube.

13. The injection needle assembly according to claim 8, wherein the fitting hole comprises a guiding wall on the inner wall near the opening of the fitting hole formed by expanding an inner diameter of the inner wall.

\* \* \* \* \*